United States Patent
Webster

(10) Patent No.: US 7,615,682 B2
(45) Date of Patent: Nov. 10, 2009

(54) DRY BEAN LINE 08550813

(75) Inventor: David M. Webster, Twin Falls, ID (US)

(73) Assignee: Seminis Vegetable Seeds, Inc., Woodland, CA (US)

( * ) Notice: Subject to any disclaimer, the term of this patent is extended or adjusted under 35 U.S.C. 154(b) by 214 days.

(21) Appl. No.: 11/674,599

(22) Filed: Feb. 13, 2007

(65) Prior Publication Data

US 2008/0196115 A1    Aug. 14, 2008

(51) Int. Cl.
*A01H 5/00*     (2006.01)
*A01H 5/10*     (2006.01)
*A01H 1/00*     (2006.01)
*C12N 5/04*     (2006.01)

(52) U.S. Cl. .................. 800/298; 800/260; 800/278; 435/410; 435/420; 435/430; 435/421

(58) Field of Classification Search .................. None
See application file for complete search history.

(56) References Cited

U.S. PATENT DOCUMENTS 6,835,876 B2 * 12/2004 Magnuson .................. 800/313

OTHER PUBLICATIONS

ADM 2006 Edible Bean Trials, 2006.
PVP Certificate for Field Bean (Phaseolus vulgaris L.) Variety EX 08550813, Apr. 15, 2008.

* cited by examiner

*Primary Examiner*—Stuart F. Baum
(74) *Attorney, Agent, or Firm*—Alissa Eagle, Esq.; Sonnenschein Nath & Rosenthal LLP

(57) ABSTRACT

The invention provides seed and plants of the dry bean line designated 08550813. The invention thus relates to the plants, seeds and tissue cultures of dry bean line 08550813, and to methods for producing a dry bean plant produced by crossing a plant of dry bean line 08550813 with itself or with another dry bean plant, such as a plant of another line. The invention further relates to seeds and plants produced by such crossing. The invention further relates to parts of a plant of dry bean line 08550813, including the pods and gametes of such plants.

23 Claims, No Drawings

DRY BEAN LINE 08550813

FIELD OF THE INVENTION

The present invention relates to the field of plant breeding and, more specifically, to the development of dry bean line 08550813.

BACKGROUND OF THE INVENTION

The goal of crop breeding is to combine various desirable traits in a single variety/hybrid. Such desirable traits may include greater yield, resistance to insects or pests, tolerance to heat and drought, better agronomic quality, higher nutritional value, growth rate and fruit or pod properties.

Breeding techniques take advantage of a plant's method of pollination. There are two general methods of pollination: a plant self-pollinates if pollen from one flower is transferred to the same or another flower of the same plant or plant variety. A plant cross-pollinates if pollen comes to it from a flower of a different plant variety.

Plants that have been self-pollinated and selected for type over many generations become homozygous at almost all gene loci and produce a uniform population of true breeding progeny, a homozygous plant. A cross between two such homozygous plants of different varieties produces a uniform population of hybrid plants that are heterozygous for many gene loci. Conversely, a cross of two plants each heterozygous at a number of loci produces a population of hybrid plants that differ genetically and are not uniform. The resulting non-uniformity makes performance unpredictable.

The development of uniform varieties requires the development of homozygous inbred plants, the crossing of these inbred plants, and the evaluation of the crosses. Pedigree breeding and recurrent selection are examples of breeding methods that have been used to develop inbred plants from breeding populations. Those breeding methods combine the genetic backgrounds from two or more plants or various other broad-based sources into breeding pools from which new lines are developed by selfing and selection of desired phenotypes. The new lines are evaluated to determine which of those have commercial potential.

One crop species which has been subject to such breeding programs and is of particular value is dry bean (*Phaseolus vulgaris* (dry)). Beans are annual, warm-season legumes. Dry beans are generally harvested as mature dry seeds, as opposed to snap beans (also known as green beans, garden beans, or pole beans) which are generally harvested when the seeds are succulent. The bean leaf is occasionally used as a leaf vegetable, and the straw is used for fodder. Some common varieties of dry bean include great northern, navy, kidney, and pinto.

The dry bean is a diploid ($2n=2x=22$) plant. Genetic improvement of dry bean has been achieved largely through the selection of varieties by applying conventional breeding techniques of self-pollinated crops. While breeding efforts to date have provided a number of useful dry bean lines with beneficial traits, there remains a great need in the art for new lines with further improved traits. Such plants would benefit farmers and consumers alike by improving crop yields and/or quality.

SUMMARY OF THE INVENTION

In one aspect, the present invention provides a dry bean plant of the line designated 08550813. Also provided are dry bean plants having all the physiological and morphological characteristics of the dry bean line designated 08550813. Parts of the dry bean plant of the present invention are also provided, for example, including pollen, an ovule, a pod, and a cell of the plant.

The invention also concerns seed of dry bean line 08550813. The dry bean seed of the invention may be provided as an essentially homogeneous population of dry bean seed of the line designated 08550813. Essentially homogeneous populations of seed are generally free from substantial numbers of other seed. Therefore, seed of line 08550813 may be defined as forming at least about 97% of the total seed, including at least about 98%, 99%, or more of the seed. The population of dry bean seed may be particularly defined as being essentially free from hybrid seed. The seed population may be separately grown to provide an essentially homogeneous population of dry bean plants designated 08550813.

In another aspect of the invention, a plant of dry bean line 08550813 comprising an added heritable trait is provided. The heritable trait may comprise a genetic locus that is, for example, a dominant or recessive allele. In one embodiment of the invention, a plant of dry bean line 08550813 is defined as comprising a single locus conversion. In specific embodiments of the invention, an added genetic locus confers one or more traits such as, for example, herbicide tolerance, insect resistance, disease resistance, and modified carbohydrate metabolism. In further embodiments, the trait may be conferred by a naturally occurring gene introduced into the genome of the line by backcrossing, a natural or induced mutation, or a transgene introduced through genetic transformation techniques into the plant or a progenitor of any previous generation thereof When introduced through transformation, a genetic locus may comprise one or more genes integrated at a single chromosomal location.

In another aspect of the invention, a tissue culture of regenerable cells of a plant of line 08550813 is provided. The tissue culture will preferably be capable of regenerating plants capable of expressing all of the physiological and morphological characteristics of the line, and of regenerating plants having substantially the same genotype as other plants of the line. Examples of some of the physiological and morphological characteristics of the line 08550813 include those traits set forth in the tables herein. The regenerable cells in such tissue cultures may be derived, for example, from embryos, meristems, cotyledons, pollen, leaves, anthers, roots, root tips, pistil, flower, seed and stalks. Still further, the present invention provides dry bean plants regenerated from a tissue culture of the invention, the plants having all the physiological and morphological characteristics of line 08550813.

In yet another aspect of the invention, processes are provided for producing dry bean seeds, plants and pods, which processes generally comprise crossing a first parent dry bean plant with a second parent dry bean plant, wherein at least one of the first or second parent dry bean plants is a plant of the line designated 08550813. These processes may be further exemplified as processes for preparing hybrid dry bean seed or plants, wherein a first dry bean plant is crossed with a second dry bean plant of a different, distinct line to provide a hybrid that has, as one of its parents, the dry bean plant line 08550813. In these processes, crossing will result in the production of seed. The seed production occurs regardless of whether the seed is collected or not.

In one embodiment of the invention, the first step in "crossing" comprises planting seeds of a first and second parent dry bean plant, often in proximity so that pollination will occur for example, mediated by insect vectors. Alternatively, pollen can be transferred manually. Where the plant is self-pollinated, pollination may occur without the need for direct human intervention other than plant cultivation.

A second step may comprise cultivating or growing the seeds of first and second parent dry bean plants into plants that bear flowers. A third step may comprise preventing self-pollination of the plants, such as by emasculating the male portions of flowers, (i.e., treating or manipulating the flowers to produce an emasculated parent dry bean plant). Self-incompatibility systems may also be used in some hybrid crops for the same purpose. Self-incompatible plants still shed viable pollen and can pollinate plants of other varieties but are incapable of pollinating themselves or other plants of the same line.

A fourth step for a hybrid cross may comprise cross-pollination between the first and second parent dry bean plants. Yet another step comprises harvesting the seeds from at least one of the parent dry bean plants. The harvested seed can be grown to produce a dry bean plant or hybrid dry bean plant.

The present invention also provides the dry bean seeds and plants produced by a process that comprises crossing a first parent dry bean plant with a second parent dry bean plant, wherein at least one of the first or second parent dry bean plants is a plant of the line designated 08550813. In one embodiment of the invention, dry bean seed and plants produced by the process are first generation ($F_1$) hybrid dry bean seed and plants produced by crossing a plant in accordance with the invention with another, distinct plant. The present invention further contemplates plant parts of such an $F_1$ hybrid dry bean plant, and methods of use thereof. Therefore, certain exemplary embodiments of the invention provide an $F_1$ hybrid dry bean plant and seed thereof In still yet another aspect of the invention, the genetic complement of the dry bean plant line designated 08550813 is provided. The phrase "genetic complement" is used to refer to the aggregate of nucleotide sequences, the expression of which sequences defines the phenotype of, in the present case, a dry bean plant, or a cell or tissue of that plant. A genetic complement thus represents the genetic makeup of a cell, tissue or plant, and a hybrid genetic complement represents the genetic make up of a hybrid cell, tissue or plant. The invention thus provides dry bean plant cells that have a genetic complement in accordance with the dry bean plant cells disclosed herein, and plants, seeds and plants containing such cells.

Plant genetic complements may be assessed by genetic marker profiles, and by the expression of phenotypic traits that are characteristic of the expression of the genetic complement, e.g., isozyme typing profiles. It is understood that line 08550813 could be identified by any of the many well known techniques such as, for example, Simple Sequence Length Polymorphisms (SSLPs) (Williams et al., 1990), Randomly Amplified Polymorphic DNAs (RAPDs), DNA Amplification Fingerprinting (DAF), Sequence Characterized Amplified Regions (SCARs), Arbitrary Primed Polymerase Chain Reaction (AP-PCR), Amplified Fragment Length Polymorphisms (AFLPs) (EP 534 858, specifically incorporated herein by reference in its entirety), and Single Nucleotide Polymorphisms (SNPs) (Wang et al., 1998).

In still yet another aspect, the present invention provides hybrid genetic complements, as represented by dry bean plant cells, tissues, plants, and seeds, formed by the combination of a haploid genetic complement of a dry bean plant of the invention with a haploid genetic complement of a second dry bean plant, preferably, another, distinct dry bean plant. In another aspect, the present invention provides a dry bean plant regenerated from a tissue culture that comprises a hybrid genetic complement of this invention.

In still yet another aspect, the invention provides a plant of an inbred pinto bean line that exhibits a combination of traits comprising resistance to race NY15 of bean common mosaic virus (BCMV) and early maturity, wherein the combination of traits may be defined as controlled by genetic means for the expression of such combination of traits found in pinto bean line 08550813.

In still yet another aspect, the invention provides a method of determining the genotype of a plant of dry bean line 08550813 comprising detecting in the genome of the plant at least a first polymorphism. The method may, in certain embodiments, comprise detecting a plurality of polymorphisms in the genome of the plant. The method may further comprise storing the results of the step of detecting the plurality of polymorphisms on a computer readable medium. The invention further provides a computer readable medium produced by such a method.

In still yet another aspect, the present invention provides a method of producing a plant derived from line 08550813, the method comprising the steps of: (a) preparing a progeny plant derived from line 08550813, wherein said preparing comprises crossing a plant of the line 08550813 with a second plant; and (b) crossing the progeny plant with itself or a second plant to produce a seed of a progeny plant of a subsequent generation. In further embodiments, the method may additionally comprise: (c) growing a progeny plant of a subsequent generation from said seed of a progeny plant of a subsequent generation and crossing the progeny plant of a subsequent generation with itself or a second plant; and repeating the steps for an additional 3-10 generations to produce a plant derived from line 08550813. The plant derived from line 08550813 may be an inbred line, and the aforementioned repeated crossing steps may be defined as comprising sufficient inbreeding to produce the inbred line. In the method, it may be desirable to select particular plants resulting from step (c) for continued crossing according to steps (b) and (c). By selecting plants having one or more desirable traits, a plant derived from line 08550813 is obtained which possesses some of the desirable traits of the line as well as potentially other selected traits.

In certain embodiments, the present invention provides a method of producing beans comprising: (a) obtaining a plant of bean line 08550813, wherein the plant has been cultivated to maturity, and (b) collecting beans from the plant.

These and other features and advantages of this invention are described in, or are apparent from, the following detailed description of various exemplary embodiments of the devices and methods according to this invention.

DETAILED DESCRIPTION OF THE INVENTION

The invention provides methods and compositions relating to plants, seeds and derivatives of dry bean line 08550813, an upright, short-vine pinto variety. Over four years of testing have shown the line to be well adapted to the Red River Valley production areas of North Dakota, Minnesota, and Manitoba. Line 08550813 shows uniformity and stability within the limits of environmental influence for the traits described hereinafter. Dry bean line 08550813 provides sufficient seed yield. By crossing with a distinct second plant, uniform F1 hybrid progeny can be obtained.

Line 08550813 exhibits a number of improved traits such as early maturity, an erect plant type, resistance to bean common mosaic virus (BCMV), and resistance to race 53 rust fungus. The erect plant type of 08550813 should facilitate "direct harvest" of this variety. Direct harvest means that, when the plants are mature, it is not be necessary to cut them and rake them into a windrow prior to threshing: they can be threshed as they stand in the field. The seed of 08550813 has less tendency to darken on exposure to moisture and light than that of other pinto varieties. The testing of this variety has been done in the Red River Valley production area of North Dakota, Minnesota, and Manitoba, but it could be grown anywhere in North America where pinto beans are planted to produce pinto seeds or to produce beans for consumption. The development of the line can be summarized as follows.

A. Origin and Breeding History of Dry Bean Line 08550813

Line 08550813 comprises traits such as early maturing, upright, and indeterminate. This pinto variety was developed by pedigree selection from a cross of breeding line, 98yt102 as seed parent, with Buster, a Seminis pinto variety, as pollen parent. Line 98yt102 was derived from a cross of P89401, a release from Michigan State University, and B311, a Seminis experimental variety. B311 had been selected from a cross of Sierra, a pinto variety developed by Michigan State University, and Topaz. The breeding history of line 08550813 can be summarized as follows:

January, Year 1 (Y1) Crossed 98yt102 and Buster in a greenhouse in Filer, Idaho.

June, Y1 Planted F1 seeds from above cross in a field in Filer, Id. Allowed the resulting plants to self pollinate.

June, Y2 Planted F2 seeds in a field in Filer, Id. Selected individual plants based on upright productive structure and desirable seed appearance.

September, Y2 Planted F3 seeds in a greenhouse in Filer, Id. Allowed the resulting plants to self pollinate.

January, Y3 Planted F4 seeds in a greenhouse in Filer, Id. Allowed the resulting plants to self pollinate.

June, Y3 Planted F5 seeds in a field in Filer, Id. Selected an individual plant based on erect, indeterminate, productive growth with seed that was uniform in size and color and that tended to resist weathering when exposed to light and moisture.

May, Y4 Panted F6 seeds (designated as R02 22700) in a field in Filer, Id. Observations during the growing season indicated that the line was uniform and stable. Trials in North Dakota that year indicated a desirable erect plant type, early maturity, uniform ripening, and good yield potential. All subsequent increases of line 08550813 trace to the bulk of R02 22700.

June, Y6 Space planted a stock of line 08550813 in a field in Filer, Id under the number RWD612. Harvested 200 individual plant selections.

May, Y7 Planted the 200 individual plant selections in a field in Filer, Id. as a progeny increase under the number RWH523. Observations during the growing season confirmed that line 08550813 is uniform and stable.

Selection criteria balanced maturity, productivity, quality and fitness for market needs, such as erect indeterminate plants, seeds that are uniform in size and color and have a reduced tendency to turn dark on exposure to light and moisture, and resistance to bean common mosaic virus and to race 53 of the rust fungus.

Observations made in Y4 and Y7 confirmed that line 08550813 is uniform and stable within commercially acceptable limits. As is true with other dry bean varieties, a small percentage of off-types can occur within commercially acceptable limits for almost any characteristic during the course of repeated multiplication. No variants are known to occur.

B. Physiological and Morphological Characteristics of Dry Bean Line 08550813

In accordance with one aspect of the present invention, there is provided a plant having the physiological and morphological characteristics of dry bean line 08550813. A description of the physiological and morphological characteristics of dry bean line 08550813 is presented below.

TABLE 1

Physiological and Morphological Characteristics* of Line 08550813

| CHARACTERISTIC | 08550813 |
|---|---|
| 1. Market Class | Pinto |
| 2. Maturity | Early (80-90 days) |
| Days from Planting to Harvest Maturity | 89 |
| 3. Plant Habit | |
| Type | Erect growth Habit-indeterminate, guides (Runners) short or not developed |
| Average Height of Mature Plant | 42 |
| Pod Position | Scattered (Not Concentrated High or Low) |
| Adaptability to Machine Harvest | Adapted |
| Lodging Resistance | Good |
| 4. Leaflet Morphology | |
| Leaflet | Wrinkled and Semi-glossy |
| Shape | Ovate |
| Apex of Leaflet | Acuminate |
| Base of Leaflet | Obtuse |
| 5. Flower Color and Days to Bloom | |
| Color of Standard | White |
| Color of Wings | White |
| Color of Keel | White |
| Days to 50% Bloom | 35 |
| 6. Pod Morphology | |
| Green Pod Color Pattern | Blotched |
| Mature Pod Color Pattern | Blotched |
| Green Pod Primary Color | Green |
| Mature Pod Primary Color | Tan |
| Green Pod Color Modifier | Light |
| Mature Pod Color Modifier | Light |
| Green Pod Secondary Color | Red |
| Mature Pod Secondary Color | Brown |
| Green Pod Cross Section Shape | Flat |
| Mature Pod Cross Section Shape | Flat |
| Green Pod Curvature | Slightly Curved |
| Mature Pod Curvature | Slightly Curved |
| Green Pod Break Orientation | Curved Downward |
| Mature Pod Break Orientation | Curved Downward |
| Average Beak Length | 1.1 cm |
| Green Pod Constrictions | Slight |
| Mature Pod Constrictions | Slight |
| Green Pod Average Number of Seeds | 5 |
| Mature Pod Average Number of Seeds | 1 |
| 7. Seed Coating/Color | |
| Texture | Semi-shiny and Monochrome |
| Color | Buff and/or Brown |
| Color Pattern | Flecked |
| Hilar Ring | Present |
| Hilar Color | Yellow |
| 8. Seed Shape and Weight | |
| Shape of Seed taken from Middle of Pod | Oval |
| Dry Weed Weight in g/100 g Seeds | 39 |
| 9. Anthocyanin Pigmentation | |
| Flowers | Absent |
| Stems | Absent |
| Pods | Present |
| Seeds | Seeds |

TABLE 1-continued

Physiological and Morphological Characteristics* of Line 08550813

| CHARACTERISTIC | 08550813 |
|---|---|
| Leaves | Absent |
| Petioles | Absent |
| Peduncles | Absent |
| Nodes | Absent |
| 10. Known Disease Reaction | |
| Bean Common Mosaic Virus | Resistant to race NY15 |
| Rust (Uromyces appendiculatus) | Resistant to race 53 |

*These are typical values. Values may vary due to environment. Other values that are substantially equivalent are within the scope of the invention.

Line 08550813 has been self-pollinated and planted for a number of generations to produce the homozygosity and phenotypic stability to make this line useful in commercial seed production. No variant traits have been observed or are expected for this line.

Dry bean line 08550813, being substantially homozygous, can be reproduced by planting seeds of the line, growing the resulting dry bean plant under self-pollinating or sib-pollinating conditions and harvesting the resulting seeds using techniques familiar to one of skill in the art.

C. Breeding Dry Bean Line 08550813

One aspect of the current invention concerns methods for crossing the dry bean line 08550813 with itself or a second plant and the seeds and plants produced by such methods. These methods can be used for propagation of line 08550813, or can be used to produce hybrid dry bean seeds and the plants grown therefrom. Hybrid seeds are produced by crossing line 08550813 with second dry bean parent line.

The development of new varieties using one or more starting varieties is well known in the art. In accordance with the invention, novel varieties may be created by crossing line 08550813 followed by multiple generations of breeding according to such well known methods. New varieties may be created by crossing with any second plant. In selecting such a second plant to cross for the purpose of developing novel lines, it may be desired to choose those plants which either themselves exhibit one or more selected desirable characteristics or which exhibit the desired characteristic(s) in progeny. Once initial crosses have been made, inbreeding and selection take place to produce new varieties. For development of a uniform line, often five or more generations of selfing and selection are involved.

Uniform lines of new varieties may also be developed by way of double-haploids. This technique allows the creation of true breeding lines without the need for multiple generations of selfing and selection. In this manner, true breeding lines can be produced in as little as one generation. Haploid embryos may be produced from microspores, pollen, anther cultures, or ovary cultures. The haploid embryos may then be doubled autonomously, or by chemical treatments (e.g. colchicine treatment). Alternatively, haploid embryos may be grown into haploid plants and treated to induce chromosome doubling. In either case, fertile homozygous plants are obtained. In accordance with the invention, any of such techniques may be used in connection with line 08550813 and progeny thereof to achieve a homozygous line.

New varieties may be created, for example, by crossing line 08550813 with any second plant and selection of progeny in various generations and/or by doubled haploid technology. In choosing a second plant to cross for the purpose of developing novel lines, it may be desired to choose those plants which either themselves exhibit one or more selected desirable characteristics or which exhibit the desired characteristic(s) in progeny. After one or more lines are crossed, true-breeding lines may be developed.

Backcrossing can also be used to improve an inbred plant. Backcrossing transfers a specific desirable trait from one inbred or non-inbred source to an inbred that lacks that trait. This can be accomplished, for example, by first crossing a superior inbred (A) (recurrent parent) to a donor inbred (non-recurrent parent), which carries the appropriate locus or loci for the trait in question. The progeny of this cross are then mated back to the superior recurrent parent (A) followed by selection in the resultant progeny for the desired trait to be transferred from the non-recurrent parent. After five or more backcross generations with selection for the desired trait, the progeny are heterozygous for loci controlling the characteristic being transferred, but are like the superior parent for most or almost all other loci. The last backcross generation would be selfed to give pure breeding progeny for the trait being transferred.

The line of the present invention is particularly well suited for the development of new lines based on the elite nature of the genetic background of the line. In selecting a second plant to cross with 08550813 for the purpose of developing novel dry bean lines, it will typically be preferred to choose those plants which either themselves exhibit one or more selected desirable characteristics or which exhibit the desired characteristic(s) when in hybrid combination. Examples of desirable characteristics may include, for example, seed yield, seed size, seed shape, seed uniformity, pod size, pod shape, pod color, pod uniformity, early maturity, disease resistance, herbicide tolerance, seedling vigor, adaptability for soil conditions, adaptability for climate conditions, and uniform plant height.

D. Performance Characteristics

As described above, line 08550813 exhibits desirable agronomic traits, such as early maturity. A variety that has some of the traits of 08550813 is the ProVita variety La Paz. One of several characteristics that distinguishes the two lines is maturity, with line 08550813 reaching maturity approximately 7 days sooner (see Table 2, below). At four trial locations in Manitoba, Canada (four replications per location), line 08550813 averaged 88.75 days to maturity, compared to 95 days for La Paz. According to the analysis of variance and the Duncan's multiple range comparison, a difference this great would have occurred less than 5% of the time had there been no real difference in maturity. These and other performance characteristics of the line were the subject of an objective analysis of the performance traits of the line relative to other lines. Results from the analysis are presented in Table 2, below.

TABLE 2

Performance Characteristics For Line 08550813

| | Filer, Idaho 2004-2006 | | | | | | | St. Thomas, North Dakota 2006 | | Morden, Manitoba 2005 | | | Morden, Manitoba 2006 3 locations | | |
|---|---|---|---|---|---|---|---|---|---|---|---|---|---|---|---|
| | Days | G/row | Sd/kg | Erect (1 = gd) | Uniformity (1 = gd) | Weathering Resistance 2004-05 (1 = gd) | Canned Quality 2004-05 20 = gd | Maturity 5 = ripe | Lbs/acre | Days | Erect 1 = gd | Kg/ha | Days | Erect 1 = gd | Kg/ha |
| Buster (Seminis) | 93.7 | 1672 | 2657 | 3.66 | 3.34 | 5.50 | 6.0 | 5.0 | 2917 | | | | 95.0 | 6.8 | 2651 |
| Windbreaker (Seminis) | 93.0 | 1600 | 2656 | 3.40 | 3.06 | 4.50 | 11.1 | 4.5 | 2348 | 109 | 4.6 | 2429 | 94.7 | 6.2 | 2668 |
| 085 5 0813 (Seminis) | 87.3 | 1704 | 2547 | 2.40 | 3.00 | 3.30 | 12.9 | 5.0 | 2888 | 103 | 3.4 | 2320 | 90.7 | 4.2 | 2416 |
| 085 4 0799 (Seminis) | | | | | | | | 5.0 | 2915 | | | | | | |
| 085 4 0800 (Seminis) | 93.0 | 1608 | 2925 | 2.86 | 2.80 | 2.70 | 14.9 | 5.0 | 2628 | | | | 93.0 | 3.8 | 2351 |
| Maverick (NDSU) | | | | | | | | 5.0 | 2364 | 108 | 6.0 | 2787 | 95.0 | 6.4 | 2444 |
| Pintoba (Canadian public) | | | | | | | | 5.0 | 2662 | 110 | 5.4 | 2537 | 99.7 | 6.2 | 2580 |
| La Paz (Provita) | | | | | | | | 5.0 | 2420 | 111 | 2.6 | 2757 | 97.3 | 4.2 | 2293 |

Subjective scales (except "Canned Quality," see above) are from 1 = good to 9 = bad.
Abbreviations defined:
"Days" is days to maturity;
"G/plot" is grams per plot, a measure of yield;
"Sd/kg" is seeds per kilogram, an inverse measure of seed size;
"Canned Quality" refers to the number of intact beans out of 20 observed;
"Erect" refers to the degree the plant grows upright, as opposed to prostrate;
"Unif" is uniformity and refers to ripening with a good score indicating that all pods are at nearly the same stage of maturity;
"Y" is year;
"gd" is good, and
"Kg/ha" is kilograms per hectare.

As shown above, line 08550813 exhibits superior characteristics, such as early maturity and erect growth, and a superior balance of characteristics when compared to competing lines. One important aspect of the invention thus provides seed of the variety for commercial use.

E. Further Embodiments of the Invention

When the term dry bean line 08550813 is used in the context of the present invention, this also includes plants modified to include at least a first desired heritable trait. Such plants may, in one embodiment, be developed by a plant breeding technique called backcrossing, wherein essentially all of the desired morphological and physiological characteristics of a variety are recovered in addition to a genetic locus transferred into the plant via the backcrossing technique. The term single locus converted plant as used herein refers to those dry bean plants which are developed by a plant breeding technique called backcrossing, wherein essentially all of the desired morphological and physiological characteristics of a variety are recovered in addition to the single locus transferred into the variety via the backcrossing technique.

Backcrossing methods can be used with the present invention to improve or introduce a characteristic into the present variety. The parental dry bean plant which contributes the locus for the desired characteristic is termed the nonrecurrent or donor parent. This terminology refers to the fact that the nonrecurrent parent is used one time in the backcross protocol and therefore does not recur. The parental dry bean plant to which the locus or loci from the nonrecurrent parent are transferred is known as the recurrent parent as it is used for several rounds in the backcrossing protocol.

In a typical backcross protocol, the original variety of interest (recurrent parent) is crossed to a second variety (nonrecurrent parent) that carries the single locus of interest to be transferred. The resulting progeny from this cross are then crossed again to the recurrent parent and the process is repeated until a dry bean plant is obtained wherein essentially all of the desired morphological and physiological characteristics of the recurrent parent are recovered in the converted plant, in addition to the single transferred locus from the nonrecurrent parent.

The selection of a suitable recurrent parent is an important step for a successful backcrossing procedure. The goal of a backcross protocol is to alter or substitute a single trait or characteristic in the original variety. To accomplish this, a single locus of the recurrent variety is modified or substituted with the desired locus from the nonrecurrent parent, while retaining essentially all of the rest of the desired genetic, and therefore the desired physiological and morphological constitution of the original variety. The choice of the particular nonrecurrent parent will depend on the purpose of the backcross; one of the major purposes is to add some commercially desirable trait to the plant. The exact backcrossing protocol will depend on the characteristic or trait being altered and the genetic distance between the recurrent and nonrecurrent parents. Although backcrossing methods are simplified when the characteristic being transferred is a dominant allele, a recessive allele may also be transferred. In this instance it may be necessary to introduce a test of the progeny to determine if the desired characteristic has been successfully transferred.

In one embodiment, progeny dry bean plants of a backcross in which 08550813 is the recurrent parent comprise (i) the desired trait from the non-recurrent parent and (ii) all of the physiological and morphological characteristics of dry bean line 08550813 as determined at the 5% significance level when grown in the same environmental conditions.

Dry bean varieties can also be developed from more than two parents. The technique, known as modified backcrossing, uses different recurrent parents during the backcrossing. Modified backcrossing may be used to replace the original recurrent parent with a variety having certain more desirable characteristics or multiple parents may be used to obtain different desirable characteristics from each.

Many single locus traits have been identified that are not regularly selected for in the development of a new inbred but that can be improved by backcrossing techniques. Single locus traits may or may not be transgenic; examples of these traits include, but are not limited to, male sterility, herbicide resistance, resistance to bacterial, fungal, or viral disease, insect resistance, restoration of male fertility, modified fatty acid or carbohydrate metabolism, and enhanced nutritional quality. These comprise genes generally inherited through the nucleus.

Direct selection may be applied where the single locus acts as a dominant trait. An example of a dominant trait is the anthracnose resistance trait. For this selection process, the progeny of the initial cross are sprayed with anthracnose spores prior to the backcrossing. The spraying eliminates any plants which do not have the desired anthracnose resistance characteristic, and only those plants which have the anthracnose resistance gene are used in the subsequent backcross. This process is then repeated for all additional backcross generations.

Selection of dry bean plants for breeding is not necessarily dependent on the phenotype of a plant and instead can be based on genetic investigations. For example, one can utilize a suitable genetic marker which is closely genetically linked to a trait of interest. One of these markers can be used to identify the presence or absence of a trait in the offspring of a particular cross, and can be used in selection of progeny for continued breeding. This technique is commonly referred to as marker assisted selection. Any other type of genetic marker or other assay which is able to identify the relative presence or absence of a trait of interest in a plant can also be useful for breeding purposes. Procedures for marker assisted selection applicable to the breeding of dry bean are well known in the art. Such methods will be of particular utility in the case of recessive traits and variable phenotypes, or where conventional assays may be more expensive, time consuming or otherwise disadvantageous. Types of genetic markers which could be used in accordance with the invention include, but are not necessarily limited to, Simple Sequence Length Polymorphisms (SSLPs) (Williams et al., 1990), Randomly Amplified Polymorphic DNAs (RAPDs), DNA Amplification Fingerprinting (DAF), Sequence Characterized Amplified Regions (SCARs), Arbitrary Primed Polymerase Chain Reaction (AP-PCR), Amplified Fragment Length Polymorphisms (AFLPs) (EP 534 858, specifically incorporated herein by reference in its entirety), and Single Nucleotide Polymorphisms (SNPs) (Wang et al., 1998).

F. Plants Derived From Dry Bean Line 08550813 by Genetic Engineering

Many useful traits that can be introduced by backcrossing, as well as directly into a plant, are those which are introduced by genetic transformation techniques. Genetic transformation may therefore be used to insert a selected transgene into the dry bean line of the invention or may, alternatively, be used for the preparation of transgenes which can be introduced by backcrossing. Methods for the transformation of plants, including dry bean, are well known to those of skill in the art. Techniques which may be employed for the genetic transformation of dry bean include, but are not limited to, electroporation, microprojectile bombardment, *Agrobacterium*-mediated transformation and direct DNA uptake by protoplasts.

As is well known in the art, tissue culture of bean can be used for the in vitro regeneration of a bean plant. Tissue culture of various tissues of beans and regeneration of plants there from is well known. For example, reference may be had to McClean and Grafton (1989); Mergeai and Baudoin (1990); Vanderwesthuizen and Groenewald (1990); Benedicic et al. (1990); Malik and Saxena (1991).

To effect transformation by electroporation, one may employ either friable tissues, such as a suspension culture of cells or embryogenic callus or alternatively one may transform immature embryos or other organized tissue directly. In this technique, one would partially degrade the cell walls of the chosen cells by exposing them to pectin-degrading enzymes (pectolyases) or mechanically wound tissues in a controlled manner.

A particularly efficient method for delivering transforming DNA segments to plant cells is microprojectile bombardment. In this method, particles are coated with nucleic acids and delivered into cells by a propelling force. Exemplary particles include those comprised of tungsten, platinum, and preferably, gold. For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate.

An illustrative embodiment of a method for delivering DNA into plant cells by acceleration is the Biolistics Particle Delivery System, which can be used to propel particles coated with DNA or cells through a screen, such as a stainless steel or Nytex screen, onto a surface covered with target dry bean cells. The screen disperses the particles so that they are not delivered to the recipient cells in large aggregates. It is believed that a screen intervening between the projectile apparatus and the cells to be bombarded reduces the size of projectiles aggregate and may contribute to a higher frequency of transformation by reducing the damage inflicted on the recipient cells by projectiles that are too large.

Microprojectile bombardment techniques are widely applicable, and may be used to transform virtually any plant species. For example, Russell et al. (1993).

*Agrobacterium*-mediated transfer is another widely applicable system for introducing gene loci into plant cells. An advantage of the technique is that DNA can be introduced into whole plant tissues, thereby bypassing the need for regeneration of an intact plant from a protoplast. Modern *Agrobacterium* transformation vectors are capable of replication in *E. coli* as well as *Agrobacterium*, allowing for convenient manipulations (Klee et al., 1985). Moreover, recent technological advances in vectors for *Agrobacterium*-mediated gene transfer have improved the arrangement of genes and restriction sites in the vectors to facilitate the construction of vectors capable of expressing various polypeptide coding genes. The vectors described have convenient multi-linker regions flanked by a promoter and a polyadenylation site for direct expression of inserted polypeptide coding genes. Additionally, *Agrobacterium* containing both armed and disarmed Ti genes can be used for transformation.

In those plant strains where *Agrobacterium*-mediated transformation is efficient, it is the method of choice because of the facile and defined nature of the gene locus transfer. The use of *Agrobacterium*-mediated plant integrating vectors to introduce DNA into plant cells is well known in the art (Fraley et al., 1985; U.S. Pat. No. 5,563,055). *Agrobacterium*-mediated transformation of *P. vulgaris* is described in, for example, Zhang et al. (1997); McClean et al. (1991); Lewis and Bliss (1994); and Song et al. (1995).

Transformation of plant protoplasts also can be achieved using methods based on calcium phosphate precipitation, polyethylene glycol treatment, electroporation, and combinations of these treatments (see, e.g., Potrykus et al., 1985; Omirulleh et al., 1993; Fromm et al., 1986; Uchimiya et al., 1986; Marcotte et al., 1988). Transformation of plants and expression of foreign genetic elements is exemplified in Choi et al. (1994), and Ellul et al. (2003).

A number of promoters have utility for plant gene expression for any gene of interest including but not limited to selectable markers, scoreable markers, genes for pest tolerance, disease resistance, nutritional enhancements and any other gene of agronomic interest. Examples of constitutive promoters useful for garden bean plant gene expression include, but are not limited to, the cauliflower mosaic virus (CaMV) P-35S promoter, which confers constitutive, high-level expression in most plant tissues (see, e.g., Odel et al., 1985), including monocots (see, e.g., Dekeyser et al., 1990; Terada and Shimamoto, 1990); a tandemly duplicated version of the CaMV 35S promoter, the enhanced 35S promoter (P-e35S) the nopaline synthase promoter (An et al., 1988), the octopine synthase promoter (Fromm et al., 1989); and the figwort mosaic virus (P-FMV) promoter as described in U.S. Pat. No. 5,378,619 and an enhanced version of the FMV promoter (P-eFMV) where the promoter sequence of P-FMV is duplicated in tandem, the cauliflower mosaic virus 19S promoter, a sugarcane bacilliform virus promoter, a commelina yellow mottle virus promoter, and other plant DNA virus promoters known to express in plant cells.

With an inducible promoter the rate of transcription increases in response to an inducing agent. Any inducible promoter can be used in the instant invention. A variety of plant gene promoters that are regulated in response to environmental, hormonal, chemical, and/or developmental signals can be used for expression of an operably linked gene in plant cells, including promoters regulated by (1) heat (Callis et al., 1988), (2) light (e.g., pea rbcS-3A promoter, Kuhlemeier et al., 1989; maize rbcS promoter, Schaffner and Sheen, 1991; or chlorophyll a/b-binding protein promoter, Simpson et al., 1985), (3) hormones, such as abscisic acid (Marcotte et al., 1989), (4) wounding (e.g., wun1, Siebertz et al., 1989); or (5) chemicals such as methyl jasmonate, salicylic acid, or Safener. It may also be advantageous to employ organ-specific promoters (e.g., Roshal et al., 1987; Schernthaner et al., 1988; Bustos et al., 1989). Exemplary organ-specific or organ-preferred promoters include, but are not limited to, a root-preferred promoter, such as that from the phaseolin gene (Sengupta-Gopalan et al., 1985); a leaf-specific and light-induced promoter such as that from cab or rubisco (Simpson et al., 1985) and Timko et al., 1985); an anther-specific promoter such as that from LAT52 (Twell et al., 1989); a pollen-specific promoter such as that from Zm13 (Guerrero et al., 1993) or a microspore-preferred promoter such as that from apg (Twell et al., 1993).

Transport of protein produced by transgenes to a subcellular compartment such as the chloroplast, vacuole, peroxisome, glyoxysome, cell wall, or mitochondroin or for secretion into the apoplast, may be accomplished by means of operably linking the nucleotide sequence encoding a signal sequence to the 5' and/or 3' region of a gene encoding the protein of interest. Targeting sequences at the 5' and/or 3' end of the structural gene may determine, during protein synthesis and processing, where the encoded protein is ultimately compartmentalized. The presence of a signal sequence directs a polypeptide to either an intracellular organelle or subcellular compartment or for secretion to the apoplast. Many signal sequences are known in the art. See, for example Becker et al. (1992); Knox et al. (1987); Lerner et al. (1989); Fontes et al. (1991); Matsuoka et al. (1991); Gould et al. (1989); Creissen et al. (1991); Kalderon et al. (1984); Steifel et al. (1990).

Exemplary nucleic acids which may be introduced to the dry bean lines of this invention include, for example, DNA sequences or genes from another species, or even genes or sequences which originate with or are present in the same species, but are incorporated into recipient cells by genetic engineering methods rather than classical reproduction or breeding techniques. However, the term "exogenous" is also intended to refer to genes that are not normally present in the cell being transformed, or perhaps simply not present in the form, structure, etc., as found in the transforming DNA segment or gene, or genes which are normally present and that one desires to express in a manner that differs from the natural expression pattern, e.g., to over-express. Thus, the term "exogenous" gene or DNA is intended to refer to any gene or DNA segment that is introduced into a recipient cell, regardless of whether a similar gene may already be present in such a cell. The type of DNA included in the exogenous DNA can include DNA which is already present in the plant cell, DNA from another plant, DNA from a different organism, or a DNA generated externally, such as a DNA sequence containing an antisense message of a gene, or a DNA sequence encoding a synthetic or modified version of a gene.

Many hundreds if not thousands of different genes are known and could potentially be introduced into a dry bean plant according to the invention. Non-limiting examples of particular genes and corresponding phenotypes one may choose to introduce into a dry bean plant include one or more genes for insect tolerance, such as a *Bacillus thuringiensis* (B.t.) gene, pest tolerance such as genes for fungal disease control, herbicide tolerance such as genes conferring glyphosate tolerance, and genes for quality improvements such as yield, nutritional enhancements, environmental or stress tolerances, or any desirable changes in plant physiology, growth, development, morphology or plant product(s). For example, structural genes would include any gene that confers insect tolerance including but not limited to a *Bacillus* insect control protein gene as described in WO 99/31248, herein incorporated by reference in its entirety, U.S. Pat. No. 5,689,052, herein incorporated by reference in its entirety, U.S. Pat. Nos. 5,500,365 and 5,880,275, herein incorporated by reference it their entirety. In another embodiment, the structural gene can confer tolerance to the herbicide glyphosate as conferred by genes including, but not limited to *Agrobacterium* strain CP4 glyphosate resistant EPSPS gene (aroA:CP4) as described in U.S. Pat. No. 5,633,435, herein incorporated by reference in its entirety, or glyphosate oxidoreductase gene (GOX) as described in U.S. Pat. No. 5,463,175, herein incorporated by reference in its entirety.

Alternatively, the DNA coding sequences can affect these phenotypes by encoding a non-translatable RNA molecule that causes the targeted inhibition of expression of an endogenous gene, for example via antisense- or cosuppression-mediated mechanisms (see, for example, Bird et al., 1991). The RNA could also be a catalytic RNA molecule (i.e., a ribozyme) engineered to cleave a desired endogenous mRNA product (see for example, Gibson and Shillito, 1997). Thus, any gene which produces a protein or mRNA which expresses a phenotype or morphology change of interest is useful for the practice of the present invention.

G. Definitions

In the description and tables herein, a number of terms are used. In order to provide a clear and consistent understanding of the specification and claims, the following definitions are provided:

A: When used in conjunction with the word "comprising" or other open language in the claims, the words "a" and "an" denote "one or more."

Allele: Any of one or more alternative forms of a gene locus, all of which alleles relate to one trait or characteristic. In a diploid cell or organism, the two alleles of a given gene occupy corresponding loci on a pair of homologous chromosomes.

Backcrossing: A process in which a breeder repeatedly crosses hybrid progeny, for example a first generation hybrid ($F_1$), back to one of the parents of the hybrid progeny. Backcrossing can be used to introduce one or more single locus conversions from one genetic background into another.

Bean Yield: A measure of productivity calculated from the weight of dry bean seeds divided by the area harvested, for example, pounds per acre, kg per hectare, grams per 10' of row, generally corrected for a standard moisture content, e.g., 10% or 12%.

Broad Adaptation: A cultivar having a broad adaptability means a cultivar or selection that will perform well in different growing conditions, locations, and seasons.

Bush Form: A USDA term about the visual look of the plant. A bean plant is: Spherical (even in width and height), Wide when the bush is wider than tall, High when the bush is taller than wide, or Stem when the individual branches protrude from the shape.

Concentrated set of pods: A concentrated set of pods refers to a plant where a high percentage of pods on a plant set and mature at the same time.

Crossing: The mating of two parent plants.

Cross-pollination: Fertilization by the union of two gametes from different plants.

Determinate plant: A determinate plant will grow to a fixed number of nodes with a terminal floral raceme on reproductive branches, while an indeterminate plant continues to grow and does not have a terminal floral raceme.

Diploid: A cell or organism having two sets of chromosomes.

Direct harvest: Normally dry beans are harvested by cutting the plants at the soil line and raking them into a "windrow" to dry, and are then combined to harvest the seeds and separate the seeds from the plant and pod material. Varieties that are suitable for direct harvest generally have erect plants and a relatively high pod set and may be combined while still standing in the field with being cut and raked into a windrow.

Dry pod color: The color of dry pods can be Buckskin (a light to pale brown), Salmon (a distinct reddish color), or Green (pale to intense) depending on the expression of the gene for persistent green.

Emasculate: The removal of plant male sex organs or the inactivation of the organs with a cytoplasmic or nuclear genetic factor conferring male sterility or a chemical agent.

Enzymes: Molecules which can act as catalysts in biological reactions.

$F_1$ Hybrid: The first generation progeny of the cross of two nonisogenic plants.

Genotype: The genetic constitution of a cell or organism.

Haploid: A cell or organism having one set of the two sets of chromosomes in a diploid.

Linkage: A phenomenon wherein alleles on the same chromosome tend to segregate together more often than expected by chance if their transmission was independent.

Marker: A readily detectable phenotype, preferably inherited in codominant fashion (both alleles at a locus in a diploid heterozygote are readily detectable), with no environmental variance component, i.e., heritability of 1.

Maturity: Number of days from planting to physiological maturity, or until the pods and seeds are sufficiently dry to be harvested with a combine. A maturity under 90 days is generally considered early while one between 90-99 days would be considered average or medium and one of 100 or more days would be late.

Phenotype: The detectable characteristics of a cell or organism, which characteristics are the manifestation of gene expression.

Pod Color: A USDA term that is applied to either green immature pods, (seed moisture of about 50%) or mature dry pods (seed moisture of about 10-15%).

Pod Position: The pod position is the location of the pods within the plant. The pods can be high (near the top), low (near the bottom), or medium (in the middle) of the plant, or scattered throughout the plant.

Quantitative Trait Loci (QTL): Quantitative trait loci (QTL) refer to genetic loci that control to some degree numerically representable traits that are usually continuously distributed.

Regeneration: The development of a plant from tissue culture.

Seed darkening: The tendency of seed of certain classes with colored seeds, such as pinto, to darken to an objectionable brown during exposure to moisture and light. Slow seed darkening is generally desirable.

Seed Size: The ratio of the weight of a number of seeds divided by the number of seeds, e.g., grams per 100 seeds.

Self-pollination: The transfer of pollen from the anther to the stigma of the same plant.

Single Locus Converted (Conversion) Plant: Plants which are developed by a plant breeding technique called backcrossing, wherein essentially all of the desired morphological and physiological characteristics of a dry bean variety are recovered in addition to the characteristics of the single locus transferred into the variety via the backcrossing technique and/or by genetic transformation.

Substantially Equivalent: A characteristic that, when compared, does not show a statistically significant difference (e.g., p=0.05) from the mean.

Tetraploid: A cell or organism having four sets of chromosomes.

Tissue Culture: A composition comprising isolated cells of the same or a different type or a collection of such cells organized into parts of a plant.

Transgene: A genetic locus comprising a sequence which has been introduced into the genome of a garden bean plant by transformation.

Triploid: A cell or organism having three sets of chromosomes.

H. Deposit Information

A deposit of dry bean line 08550813, disclosed above and recited in the claims, has been made with the American Type Culture Collection (ATCC), 10801 University Blvd., Manassas, Va. 20110-2209. The date of deposit was Jan. 8, 2007. Upon issuance of a patent, all restrictions upon the deposit will be removed, and the deposit is intended to meet all of the requirements of 37 C.F.R. §1.801-1.809. The accession number for those deposited seeds of dry bean line 08550813 is ATCC Accession No. PTA-8114. The deposit will be maintained in the depository for a period of 30 years, or 5 years after the last request, or for the effective life of the patent, whichever is longer, and will be replaced if necessary during that period.

Although the foregoing invention has been described in some detail by way of illustration and example for purposes of clarity and understanding, it will be obvious that certain changes and modifications may be practiced within the scope of the invention, as limited only by the scope of the appended claims.

All references cited herein are hereby expressly incorporated herein by reference.

REFERENCES

The following references, to the extent that they provide exemplary procedural or other details supplementary to those set forth herein, are specifically incorporated herein by reference:

U.S. Pat. No. 5,463,175
U.S. Pat. No. 5,500,365
U.S. Pat. No. 5,563,055
U.S. Pat. No. 5,633,435
U.S. Pat. No. 5,689,052
U.S. Pat. No. 5,880,275
U.S. Pat. No. 5,378,619
An et al., *Plant Physiol.*, 88:547, 1988.
Becker et al., *Plant Mol. Biol.*, 20:49, 1992.
Benedicic et al., *Plant Cell Tissue Org. Cult.*, 24:199-206, 1990.
Bird et al., *Biotech. Gen. Engin. Rev.*, 9:207, 1991.
Bustos et al., *Plant Cell*, 1:839, 1989.
Callis et al., *Plant Physiol.*, 88:965, 1988.
Choi et al., *Plant Cell Rep.*, 13: 344-348, 1994.
Creissen et al., *Plant J.*, 2:129, 1991.
Dekeyser et al., *Plant Cell*, 2:591, 1990.
Ellul et al., *Theor. Appl. Genet.*, 107:462-469, 2003.
EP 534 858
Fontes et al., *Plant Cell*, 3:483-496, 1991.
Fraley et al., *Bio/Technology*, 3:629-635, 1985.
Fromm et al., *Nature*, 312:791-793, 1986.
Fromm et al., *Plant Cell*, 1:977, 1989.
Gibson and Shillito, *Mol. Biotech.*, 7:125,1997
Gould et al., *J. Cell. Biol.*, 108:1657, 1989.
Guerrero et al., *Mol. Gen. Genetics*, 244:161-168, 1993.
Kalderon et al., *Cell*, 39:499-509, 1984.
Klee et al., *Bio-Technology*, 3(7):637-642, 1985.
Knox et al., *Plant Mol Biol.*, 9:3-17, 1987.
Kuhlemeier et al., *Plant Cell*, 1:471, 1989.
Lemer et al., *Plant Physiol.*, 91:124-129, 1989.
Lewis and Bliss, *J. American Soc. Horticul. Sci.*, 119:361-366, 1994.
Malik, and Saxena, *Planta*, 184(1):148-150, 1991.
Marcotte et al., *Nature*, 335:454, 1988.
Marcotte et al., *Plant Cell*, 1:969, 1989.
Matsuoka et al., *Proc. Natl. Acad. Sci. USA*, 88:834, 1991.
McClean and Grafton, *Plant Sci.*, 60:117-122, 1989.
McClean et al, *Plant Cell Tiss. Org. Cult.*, 24:131-138, 1991.
Mergeai and Baudoin, *B.I.C. Invit. Papers*, 33:115-116, 1990.
Odel et al., *Nature*, 313:810, 1985.
Omirulleh et al., *Plant Mol. Biol.*, 21(3):415-428, 1993.
Potrykus et al., *Mol Gen. Genet.*, 199:183-188, 1985.
Roshal et al., *EMBO J.*, 6:1155, 1987.
Russell et al., *Plant Cell Reports*, 12(3):165-169 (1993.
Schaffner and Sheen, *Plant Cell*, 3:997, 1991.
Schernthaner et al., *EMBO J.*, 7:1249, 1988.
Sengupta-Gopalan et al., *Proc. Natl. Acad. Sci. USA*, 82:3320-3324, 1985.
Siebertz et al., *Plant Cell*, 1:961, 1989.
Simpson et al., *EMBO J.*, 4:2723, 1985.
Song et al., *J. Plant Physiol.*, 146:148-154, 1995.
Steifel et al., *Plant Cell*, 2:785-793, 1990.
Terada and Shimamoto, *Mol. Gen. Genet.*, 220:389, 1990.
Timko et al., *Nature*, 318:579-582, 1985.
Twell et al, *Mol Gen. Genetics*, 217:240-245, 1989.
Twell et al, *Sex. Plant Reprod.*, 6:217-224, 1993.
Uchimiya et al., *Mol. Gen. Genet.*, 204:204, 1986.
Vanderwesthuizen and Groenewald, *S. Afr. J. Bot.*, 56:271-273, 1990.
Wang et al., *Science*, 280:1077-1082, 1998.
Williams et al., *Nucleic Acids Res.*, 18:6531-6535, 1990.
WO 99/31248
Zhang et al., *J. American Soc. Horticul. Sci.*, 122(3):300-305, 1997.

What is claimed is:

1. A seed of dry bean line 08550813, wherein a sample of seed of dry bean line 08550813 has been deposited under ATCC Accession Number PTA-8114.

2. A plant of dry bean line 08550813, wherein a sample of seed of dry bean line 08550813 has been deposited under ATCC Accession Number PTA-8114.

3. A plant part of the plant of claim 2.

4. The plant part of claim 3, wherein said part is selected from the group consisting of a pod, pollen, an ovule and a cell.

5. A dry bean plant, or a part thereof, having all the physiological and morphological characteristics of the dry bean plant of claim 2.

6. A tissue culture of regenerable cells of dry bean line 08550813, wherein a sample of seed of dry bean line 08550813 has been deposited under ATCC Accession Number PTA-8114.

7. The tissue culture according to claim 6, comprising cells or protoplasts from a plant part selected from the group consisting of embryos, meristems, cotyledons, pollen, leaves, anthers, roots, root tips, pistil, flower, seed and stalks.

8. A dry bean plant regenerated from the tissue culture of claim 6, wherein the regenerated plant comprises all of the physiological and morphological characteristics of dry bean line 08550813, wherein a sample of seed of dry bean line 08550813 has been deposited under ATCC Accession Number PTA-8114.

9. A method of producing dry bean seed, comprising crossing the plant of claim 2 with itself or a second dry bean plant.

10. The method of claim 9, wherein the plant of dry bean line 08550813 is the female parent.

11. The method of claim 9, wherein the plant of dry bean line 08550813 is the male parent.

12. An F1 hybrid seed produced by the method of claim 9.

13. An F1 hybrid plant produced by growing the seed of claim 12.

14. A method for producing a seed of a line 08550813-derived dry bean plant comprising the steps of:
  (a) crossing a dry bean plant of line 08550813, wherein a sample of seed of dry bean line 08550813 has been deposited under ATCC Accession Number PTA-8114, with a second dry bean plant; and
  (b) allowing seed of a 08550813-derived dry bean plant to form.

15. The method of claim 14, further comprising the steps of:
  (c) crossing a plant grown from said 08550813-derived dry bean seed with itself or a second dry bean plant to yield additional 08550813-derived dry bean seed;
  (d) growing said additional 08550813-derived dry bean seed of step (c) to yield additional 08550813-derived dry bean plants; and
  (e) repeating the crossing and growing steps of (c) and (d) to generate further 08550813-derived dry bean plants.

16. A method of vegetatively propagating a plant of dry bean line 08550813 comprising the steps of:
  (a) collecting tissue capable of being propagated from a plant of dry bean line 08550813, wherein a sample of seed of dry bean line 08550813 has been deposited under ATCC Accession Number PTA-8114;
  (b) cultivating said tissue to obtain proliferated shoots; and
  (c) rooting said proliferated shoots to obtain rooted plantlets.

17. The method of claim 16, further comprising growing plants from said rooted plantlets.

18. A method of introducing a desired trait into dry bean line 08550813 comprising:
  (a) crossing a plant of line 08550813, wherein a sample of seed of dry bean line 08550813 has been deposited under ATCC Accession Number PTA-811411, with a second dry bean plant that comprises a desired trait to produce F1 progeny;
  (b) selecting an F1 progeny that comprises the desired trait;
  (c) crossing the selected F1 progeny with a plant of line 08550813, wherein a sample of seed of dry bean line 08550813 has been deposited under ATCC Accession Number PTA-8114, to produce backcross progeny;
  (d) selecting backcross progeny comprising the desired trait and the physiological and morphological characteristic of dry bean line 08550813; and
  (e) repeating steps (c) and (d) three or more times in succession to produce selected fourth or higher backcross progeny that comprise the desired trait and all of the physiological and morphological characteristics of dry bean line 08550813 when grown in the same environmental conditions.

19. A dry bean plant produced by the method of claim 18.

20. A method of producing a plant of dry bean line 08550813, wherein a sample of seed of dry bean line 08550813 has been deposited under ATCC Accession Number PTA-8114, comprising an added desired trait, the method comprising introducing a transgene conferring the desired trait into a plant of dry bean line 08550813.

21. A progeny plant of the plant of claim 1, wherein the plant expresses all of the physiological and morphological characteristics of dry bean line 08550813, and wherein a sample of seed of said dry bean line has been deposited under ATCC Accession Number PTA-8114.

22. A seed that produces the plant of claim 21.

23. A method of producing beans comprising:
  (a) obtaining the plant of claim 2, wherein the plant has been cultivated to maturity, and
  (b) collecting beans from the plant.

* * * * *